United States Patent [19]

Newkirk et al.

[11] 4,372,815

[45] Feb. 8, 1983

[54] METHOD FOR UPGRADING PAPER AND THE PRODUCT FORMED THEREBY

[75] Inventors: David D. Newkirk, Beaverton, Oreg.; Darrel L. Wilhoit, Wadsworth, Ill.

[73] Assignee: Crown Zellerbach Corporation, San Francisco, Calif.

[21] Appl. No.: 293,075

[22] Filed: Aug. 17, 1981

[51] Int. Cl.³ .............................................. D21H 3/02
[52] U.S. Cl. ........................................ 162/158; 8/100
[58] Field of Search ............................ 162/158; 8/190

[56] References Cited

U.S. PATENT DOCUMENTS 3,961,892 6/1976 Bishop et al. ........................... 8/190

FOREIGN PATENT DOCUMENTS 1226459 7/1960 France ..................................... 8/19

Primary Examiner—William F. Smith

[57] ABSTRACT

This invention is directed to a method for upgrading cellulose by treating same with a chemical to produce a cellulose sheet having substantially increased absorbency, bulk and softness properties. The chemical system comprises the reaction product of a cyanuric halide compound and an alkylene oxide compound, respectively.

8 Claims, No Drawings

4,372,815

METHOD FOR UPGRADING PAPER AND THE PRODUCT FORMED THEREBY

BACKGROUND OF THE INVENTION

In the production of standard grades of paper on a conventional paper machine, cellulose fibers and water are combined in a headbox to form an aqueous fiber furnish. A wet fibrous web is then formed on the papermaking wire, and the water is mechanically removed from the web. This mechanical dewatering step increases the consistency of the web from about 5%, the consistency on formation, up to about 40%, or more. As the water is mechanically displaced from the web, the fibers forming the web are moved into close proximity with each other. Chemical papermaking bonds, generally described as hydrogen bonds, are formed between adjacent surfaces of a substantial number of the cellulose fibers. The formation of these hydrogen bonds serves to strengthen the web, as measured, for example, by a substantial increase in the physical strength properties of the web.

The uncontroled formation of substantial numbers of hydrogen bonds between the surfaces of adjacent fibers is, however, detrimental to paper properties such as absorbency, bulk and softness which are critical in certain grades of tissue and towel. Therefore, conventional papermaking, as described above, cannot readily be employed in this latter application where high quality products are described.

In an attempt to upgrade conventionally formed paper and to produce a paper product having increased absorbency, bulk, and softness properties, certain prior art methods treat cellulose with chemical "debonding agents". For instance, U.S. Pat. Nos. 3,812,000 to Salvucci et al; 3,844,880 to Meisel et al.; and 3,903,342 to Roberts et al., respectively, as well as pending applications U.S. Ser. Nos. 99,041 and 176,225, assigned to the assignee of the present invention, describe improving the softness of cellulose employing various debonding agents. Typical debonding agents used are fatty, long-chain amine compounds. The most effective of these materials are the cationic compounds typified by quaternary amines such as described in Hervey et al., U.S. Pat. Nos. 3,554,862; 3,554,863; and 3,395,708.

The above described effect in paper is quite different from, for example, the "softening" effect in textile fibers. In the case of textiles, the surface is made soft to the touch and is, in essence, "lubricated". However, these textiles maintain a very high level of internal strength since this is a requirement of textile fabrics. Neither bulk nor absorbency of the textiles is substantially increased. The softening effect is contrary to the effect in the previously described high absorbency and bulk applications wherein the mechanical strength properties of the sheet are modified. Patents such as U.S. Pat. Nos. 3,104,935 to Moyse; 3,124,414 to Dolmetsch; 3,057,675 to Hiestand; and 3,847,915 and 3,961,892 to Bishop et al. describe the use of various 1,3,5-triazine ring materials as softening compounds for textile materials. In an article in the 1971 Australian Journal of Chemistry, Volume 24, pages 26, 49–54, the preparation of triazinyl compound, i.e., bis(dichlorotriazinyl) derivatives of diethylene and triethylene glycol, for application to wool, is described by Ayscough et al.

The reaction of cyanuric chloride with cellulose has also been described in U.S. Pat. Nos. 1,886,480 to Haller et al.; 2,892,674 to Sause; 4,035,146 to Brenner et al.; and various journal articles including "Action of Cyanuric Chloride on Cotton Cellulose", by Warren et al., in Textile Research Journal, September 1952; and a series of articles by Allan et al., including "Fiber Surface Modification, Part IV. The Reactivity of Lignocellulosic Fibers with Cyanuric Chloride", in Volume 53, No. 8, of TAPPI, August 1970; and "Fiber Surface Modification. Part XIII. Constitutive Fiber Parameters for the Reaction of Pulps with Cyanuric Chloride", in Specialnummer 4a, Papper och Tra (1972).

British Pat. No. 1,131, 762 to Colgate-Palmolive Company is directed to the use of large amounts, i.e., 5% to 50%, of a poly(ethylene oxide) compound having an average molecular weight in the range of 280 to 810 as an internal plasticizer.

Other softening agents for fibers include an emulsion of chlorocyanuric acid and a fatty acid. This emulsion is used for cotton and rayon fibers and is described in Japanese Pat. No. 74-40,035.

SUMMARY OF THE INVENTION

This invention is directed to a method for upgrading paper products and to the product formed thereby. The subject method for upgrading paper products is quite different from the methods set forth in the prior art, especially in the previously described textile art. In the case of textiles, only surface lubrication of the surface of the fibers is effected. In the present invention, on the other hand, not only is the total softness of the paper increased, but substantial increases in the absorbency and bulk properties are also manifested.

A cyanuric halide such as cyanuric chloride improves the surface feel of paper at moderate additional levels. At the same addition level, poly(ethylene oxide) per se provides substantially no improvement in softness properties.

For purposes of illustration, an experiment was conducted (see Example 1C) in which cellulose was "sequentially" treated with cyanuric chloride and poly(ethylene oxide) at a total addition level equal to the above addition level of cyanuric chloride or poly(ethylene oxide) per se. Sequential treatment involves first treating cellulose with a cyanuric chloride compound, in this case cyanuric chloride, followed by reacting the treated cellulose product with an alkylene oxide compound, in this case poly(ethylene oxide). The above described sequential treatment is not disclosed in the prior art. This sequential method produces a treated cellulose sheet which exhibits a level of absorbency, bulk, and softness only marginally better than its untreated counterpart.

However, quite unexpectedly, when the same total amount of the reaction product of cyanuric halide, i.e., cyanuric chloride and polyalkylene oxide, i.e., poly(ethylene oxide), in the same molecular ratio, are first reacted one with the other, and this reaction product is then subsequently combined with cellulose in the formation of a paper product, a substantial, unexpected increase results in the absorbency, bulk, and softness of the paper formed thereby (see Examples 1D and 1E).

The specific products formed by the reaction of a cyanuric halide and a polyalkylene oxide compound are mixtures of monomers, oligimers, and polymers, which are extremely difficult to separate from each other and analyze. It is believed that the general structural formula for the major product of the above reaction is, however, as hereinafter described.

Nowhere in the prior art can one find a suggestion of the "sequential" reaction of cyanuric halide and a polyalkylene oxide compound with cellulose to form an absorbent, bulky, and soft paper product. And beyond the above sequential reaction, there is certainly no prior art description directed to the reaction and subsequent combination of the reaction product of a cyanuric halide and a polyalkylene oxide compound for use in the formation of absorbent, bulky, and soft paper products. The result described in Examples 1D and 1E are particularly unexpected since it is generally accepted practice that if, argumento, one were to combine a cyanuric halide and a polyalkylene oxide compound with cellulose, one would sequentially react each chemical component directly with the cellulose in order to maximize the number of reactive sites during each of the chemical reactions. Since the sequential reaction process only minimally improves the degree of absorbency, bulk, and softness of the paper (see Example 1C), one would expect that the absorbency, bulk, and softness of paper produced using the reaction product of a cyanuric halide compound and a polyalkylene oxide compound in combination with cellulose would exhibit an even further diminished level of the above described paper properties. Contrarily, however, it has been unexpectedly found that when the method of the present invention is employed, an increase in absorbency, bulk, and softness properties (see Example 1D and 1E), is actually provided.

DETAILED DESCRIPTION OF THE INVENTION

As hereinafter described in the preferred embodiment of this invention, an aqueous furnish, including cellulosic papermaking fibers, is initially formed. These cellulosic fibers have undergone some degree of lignin modification such as at least partial chemical treatment to produce materials such as chemimechanical pulp, semichemical pulp, chemical pulp, or mixtures thereof. Suitable materials from which the above cellulosic fibers can be derived include the usual species of coniferous and deciduous pulpwood, the cellulosic components being preferably produced from coniferous pulpwood because of its greater fiber length. The aqueous furnish is then transported to a paper machine headbox at a consistency level sufficient to permit the formation of a substantially dried sheet on completion of the hereinafter described dewatering and thermal drying steps, respectively, without requiring further drying thereof subsequent to creping. As a practical matter, however, consistency of the aqueous furnish is used in forming a subject wet web and is desirably maintained at a level of about 0.05% by weight, more preferably 0.1% by weight, based on the total weight of cellulosic fibers in the aqueous furnish, up to a preferred consistency of about 1.0% by weight, and more preferably up to about 0.75% by weight.

A chemical treatment system comprising the reaction product of a cyanuric halide compound and a polyalkylene oxide compound, respectively, is employed to treat cellulosic fibers. This treatment system is preferably combined with the cellulose in the aqueous furnish prior to web formation. Cyanuric chloride and bromide are the preferred cyanuric halide compounds, with the chloride being the most preferred. The preferred cyanuric chloride compound is a halogenated 1,3,5-triazine compound, the most preferred cyanuric chloride compound being 2,4,6-trichloro-1,3,5-triazine.

The chemical system employed for treatment of the cellulosic papermaking fibers comprises the reaction product of the previously described cyanuric halide and a second compound which is a polyalkylene oxide material. The polyalkylene oxide preferably comprises a compound having an alkylene linkage, either straight chain or branched, from two to six carbon atoms, preferably two to four carbon atoms, more preferably two to three carbon atoms, and most preferably two carbon atoms, including materials such as poly(ethylene oxide), poly(propylene oxide), or combinations thereof, poly(butylene oxide), and poly(tetrahydrofuran). Other substituted alkylene oxide compounds include alkyl-substituted having one to twelve carbon atoms, preferably methyl, ethyl, n-propyl, isopropyl, butyl, hexyl, octyl, decyl, and dodecyl; cycloalkyl-substituted having one to twelve carbon atoms; aryl-substituted having one to fifteen carbon atoms, preferably phenyl, tolyl, xylyl, propylphenyl, butylphenyl, octyl phenyl, and nonyl phenyl; and triazinyl-substituted preferably mono-, di- and trichlorotriazinyl, and most preferably 4,6-dichlorotriazinyl, and 2,4,6-trichloro-1,3,5-triazinyl. However, the most preferred polyalkylene oxide compound is poly(ethylene oxide) due to its ready availability and low cost.

The polyalkylene oxide compounds employed herein are preferably low molecular weight compounds having a molecular weight of from about 100, and more preferably from about 125, and most preferably from about 150, up to preferably about 1,500, and more preferably up to about 1,200, and most preferably up to about 800. An example of preferred poly(ethylene oxide) materials are PLURACOL E compounds, manufactured by BASF Wyandotte.

Cyanuric halide compound and polyalkylene oxide compound are preferably reacted one with the other in a ratio such that one mole of cyanuric halide is combined with one mole of active terminal hydroxyl group present in the polyalkylene oxide. This ratio assures the complete reaction of the respective chemical components for optimum chemical treatment without having a substantial excess of either material.

For the reasons previously set forth, the reaction product mixture has not been fully identified, but the major product of the cyanuric halide-polyalkylene oxide reaction is believed to be a chemical composition having the following general structure:

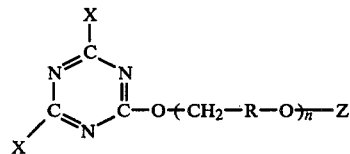

in which X represents halogen, preferably chlorine or bromide and most preferably chlorine; R represents an alkylene group, either straight chain or branched, having from one to five carbon atoms, preferably one to three carbon atoms and more preferably from one to two carbon atoms; and Z is a terminal end group capable of capping off the alkylene oxide constituent such as an alkyl group having one to twelve carbon atoms, preferably methyl, ethyl, n-propyl, isopropyl, butyl, hexyl, octyl, decyl, or dodecyl; a cycloalkyl group having one to twelve carbon atoms; an aryl group having one to fifteen carbon atoms, preferably phenyl, tolyl, xylyl, propylphenyl, butylphenyl, octyl phenyl, or nonyl phenyl; and substituted triazinyl group, preferably chlorotriazinyl, dichlorotriazinyl, more preferably chloro- and 4,6-dichloro-1,3,5-triazinyl.

Preferably, n is from about 2, and more preferably from about 3, and most preferably from about 4, up to preferably about 30, and more preferably up to about 25, and most preferably up to about 12.

The amount of reaction product added to the aqueous furnish will vary, depending on the required degree of absorbency, bulk, and softness. Preferably, however, a sufficient amount of the reaction product should be added to the pulp so that at least about $0.5 \times 10^{-5}$ mole of reaction product per gram of pulp is retained by the subject cellulosic paper sheet product. More preferably, from about $1.0 \times 10^{-5}$ moles of reaction product and most preferably from about $3.0 \times 10^{-5}$ moles of reaction product per gram of pulp are retained on the sheet product. The maximum amount of the chemical system is determined by factors such as cost and minimum physical strength of the sheet.

A wet web is then formed by deposition of the aqueous furnish onto a wet-forming means, typically a conventional papermaking system including a foraminous conveying means such as a Fourdrinier wire, a Stevens former, or the like.

Dewatering of the wet web containing the chemical system, after the chemical system is added to the furnish, is then provided prior to the thermal drying operation, typically employing nonthermal dewatering means. The nonthermal dewatering step is usually accomplished by various means for imparting mechanical compaction to the web such as vacuum boxes, slot boxes, coacting press rolls, or combinations thereof.

The wet web is carried by the foraminous conveying means through the nonthermal dewatering means wherein it is dewatered to a consistency of at least about 5%, preferably at least about 10%, and more preferably to at least 15%, up to a consistency of preferably about 50%, and more preferably up to about 45%, and most preferably up to about 35%.

The wet web, prior to thermal drying step, can be treated with the previously described chemical system by various techniques including spraying the material onto the web on-line. Treatment of the wet web with a chemical treatment system, instead of, or in addition to, the aqueous furnish treatment step, can also be provided. For instance, the treatment step can comprise treatment of the wet web by spraying, applying with a direct contact applicator means, or by employing an applicator felt. However, the preferred method of application is by spraying the web such as by employing a spray nozzle system at various points prior to the thermal drying means. The material employed for treatment of the web is provided at a treatment level which is sufficient to minimize the formation of the previously described hydrogen bonds so that the requisite absorbence, bulk, and softness levels are maintained, but less than an amount which would cause significant runnability and sheet-strength problems in the final commercial product.

The treated web is then applied to the surface of the thermal drying means, preferably a thermal drying cylinder such as a Yankee drying cylinder. Preferably, an adhesive is employed to supplement the adhesion process. Examples of typical adhesive compounds which may be used include carboxymethyl cellulose, polyvinyl alcohol, anionic starch, various soluble natural polymers such as gums, and the like, and synthetic resins such as polyamide resins, and the like. Adhesion of the treated web to the cylinder surface is preferably facilitated by the mechanical compression and action exerted thereon such as by using one or more press rolls, which form a nip in combination with the thermal drying means and brings the web into more uniform contact with the thermal drying surface.

The web is then dried on the thermal drying surface preferably to a consistency of at least about 92%, and more preferably to a consistency of about 95%, and most preferably to a consistency of about 97%.

A creping step is then preferably conducted. The web is removed, in the creping step, from the thermal drying surface by the creping action causing disruption of the bonds between the respective fibers. This provides a softening effect to be imparted to the web to produce the subject sheet product. In general, the creping means is a doctor blade which crepes and removes the web from the thermal drying surface.

The product sheet has a high degree of softness. "Softness" is measured by conducting a Handle-O-Meter test (HOM) according to TAPPI T-498. The softness (reciprocal of stiffness) of a given sheet is calculated by dividing the HOM value by the square of the caliper of a given single sheet being treated, the quotient thereof being multiplied by $10^{-5}$, whereby the smaller the softness values, the greater the softness.

Another important sheet property is the ability to absorb liquids, particularly water. The water absorbency parameter is expressed as the number of seconds it takes for a single sheet (4.5 inches by 4.5 inches) to absorb 0.1 cc of water, as described in TAPPI T-432.

By employing the novel method of the present invention, a paper product is produced which exhibits an unexpected substantial increase in the water absorbency property. If the present method of this invention is employed, as opposed to the prior art systems previously discussed, an increase in water absorbency will be provided of at least about 2.25 times, and more preferably at least about 2.50 times; and most preferably at least about 2.75 times that of its untreated counterparts.

The bulkiness of the paper sheet product is also unexpectedly higher when the subject method is employed. Bulk is determined by measuring the caliper in mils of a single sheet. This is done by making such caliper measurements, known as Lobb caliper, wherein five test sheets are subjected to a force imparted by a four-inch-diameter iron cylinder. The measured value is then read, and the reading divided by five in order to determine the caliper of a single sheet. A total pressure of about 1.35 kg/cm$^2$ is imparted to the sheets by the cylinder. Preferably, the rate of increase in the Lobb caliper of the treated paper sheet is provided of at least about 1.25 times that of its untreated counterpart.

EXAMPLE 1

A series of experiments was conducted in which a given amount of various chemical treatment systems were compared on the basis of the absorbency, bulk, and softness of paper sheets produced therefrom. The method employed in each of these experiments is as follows:

The chemical treatment system consisted of adding a solution of 2.5 grams of the chemical treatment compounds employed, dissolved in 50 ml of acetone, to a mixture of 40 grams of pulp (25% total solids), and 160 grams of water. The mixture of chemicals and pulp was mixed by hand for two minutes, allowed to stand for an additional eight minutes, and then treated with sufficient sodium carbonate solution to achieve a pH of 10.5. After allowing the pulp to soak in the chemicals for thirty minutes, it was filtered, then washed with 1,000 ml of acetone and 1,000 ml of water. The pulp cake was dispersed with a Waring Blendor into water, and handsheets were made therefrom, and tested.

Experiments 1A and 1B, respectively, employed cyanuric chloride per se and poly(ethylene oxide) per se. Experiment 1C is directed to the sequential addition of cyanuric chloride to a cellulose furnish, followed by reacting poly(ethylene oxide) therewith. A molecular ratio of 2:1 is maintained between the cyanuric chloride and polyalkylene oxide. Experiments 1D and 1E were conducted using the reaction product of cyanuric chloride and poly(ethylene oxide), in the same molecular ratio. Both a 200 molecular weight (1D) and a 400 molecular weight (1E) poly(ethylene oxide) compound PLURACOL E200 and E400, respectively, were employed.

The cyanuric chloride-poly(ethylene oxide) reaction products of Experiments 1D and 1E were prepared by forming a solution of the poly(ethylene oxide) and 2,4,6-collidine dissolved in 400 ml of acetone. The solution was then cooled to about 3° C., and the cyanuric chloride dissolved in acetone was added thereto over a period of about 1.5 to 2 hours. After stirring for about 12 hours and warming to room temperature, the solution was filtered, the solvent was substantially removed by vacuum evaporation, and the product recovered after a final filtration step.

The results of these experiments are summarized in Table I.

TABLE I

|  | CONTROL | A | B | C | D | E |
|---|---|---|---|---|---|---|
| Water Absorbency (Secs) | 30.85* 30.40** | 13.98 | 28.75 | 19.40 | 8.16 | 11.05 |
| Rate of Increase in Water Absorbency | 1.00 | 2.17 | 1.07 | 1.56 | 3.78 | 2.79 |
| Lobb Caliper (Mils) | 4.00* 4.20** | 4.90 | 4.20 | 4.60 | 5.40 | 5.00 |
| Rate of Increase in Lobb Caliper | 1.00 | 1.17 | 1.10 | 1.10 | 1.35 | 1.25 |
| Softness | 4.34* 4.07** | 2.66 | 4.07 | 3.11 | 1.90 | 2.63 |
| Rate of Increase in Softness | 1.00 | 1.53 | 1.06 | 1.31 | 2.28 | 1.65 |

*Control for Runs B, D, and E
**Control for Runs A and C

The results manifested in Table I relating to absorbency, bulk, and softness follow a clearly defined pattern. In Run A, a sheet was formed by treating cellulose with one part (2.5 grams) of cyanuric chloride. An improvement in the absorbency, bulk, and softness with respect to an untreated sheet is indicated by the data. In Run B, a sheet was produced by treating cellulose with one part of poly(ethylene oxide) having a molecular weight of 200. The rate of increase in sheet properties set out in Table I, for the sheet produced in Run B, is negligible.

The data for the sheet produced from cellulose treated with a total of one part of cyanuric chloride and poly(ethylene oxide), respectively, produced by sequential reaction with cellulose (Run C), indicates that the rate of increase of absorbency, bulk, and softness falls between the rate of increase for the sheet produced in Runs A and B, respectively. Thus, the use in Run C of poly(ethylene oxide) in place of a substantial portion of the cyanuric chloride causes a dramatic reduction in the absorbency, bulk, and softness properties of the resultant treated cellulose sheet when compared to the results of Run A.

In Runs D and E, a total of one part of cyanuric chloride and poly(ethylene oxide) in the same molecular ratio as in Run C, was employed as the source of chemical treatment. As previously stated, instead of employing the sequential addition method, the cyanuric chloride and poly(ethylene oxide) were reacted one with the other, and reaction product used to treat the cellulose. A dramatically unexpected increase in the rate of absorbency, bulk, and softness was provided in sheet products made in Runs D and E.

We claim:

1. A method for upgrading cellulose sheets by substantially increasing the absorbency, bulk, and softness thereof, which comprises treating cellulose with a chemical compound having the following general formula:

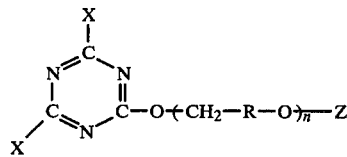

in which X represents halogen; R represents an alkylene group, either straight chain or branched, having from one to five carbon atoms; n is from about 2 up to about 30; and Z is a halogen substituted 1,3,5-triazinyl group.

2. The method of claim 1, wherein X represents chlorine.

3. The method of claim 1, wherein R represents an alkylene group having one to two carbon atoms.

4. The method of claim 2, wherein R is an alkylene group having one carbon atom, and Z is a 4,6-dichloro-1,3,5-triazinyl group.

5. An absorbent, bulky, and soft cellulose sheet which comprises cellulose which has been treated with a chemical compound having the following general formula:

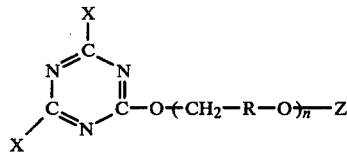

in which X represents halogen; R represents an alkylene group, either straight chain or branched, having from one to five carbon atoms; n is from about 2 up to about 30; and Z is a halogen substituted 1,3,5-triazinyl group.

6. The product of claim 5, wherein X represents chlorine.

7. The product of claim 5, wherein R represents an alkylene group having one to two carbon atoms.

8. The product of claim 6, wherein R is an alkylene group having one carbon atom, and Z is a 4,6-dichloro-1,3,5-triazinyl group.

* * * * *